United States Patent [19]

Morin et al.

[11] Patent Number: 4,556,074
[45] Date of Patent: Dec. 3, 1985

[54] DENTAL FLOSSING TOOL

[75] Inventors: Marius J. Morin, Westlake Village; Jack C. Munro, Thousand Oaks, both of Calif.

[73] Assignee: Associated Medical Systems, Inc., Agoura Hills, Calif.

[21] Appl. No.: 545,890

[22] Filed: Oct. 27, 1983

Related U.S. Application Data

[63] Continuation-in-part of Ser. No. 413,682, Sep. 1, 1982, abandoned.

[51] Int. Cl.[4] .............................................. A61C 15/00
[52] U.S. Cl. ................................................ 132/92 R
[58] Field of Search ................... 132/89, 90, 91, 92 R, 132/92 A, 93; 206/53, 478, 480, 483; 242/137, 137.1, 138; 24/3 F, 3 M; 401/36, 44, 47, 140

[56] References Cited

U.S. PATENT DOCUMENTS

| | | | |
|---|---|---|---|
| 810,292 | 1/1906 | Meaker | 206/53 |
| 1,712,686 | 5/1959 | Bornmann | 206/480 |
| 2,013,143 | 9/1935 | Getz | 132/92 R |
| 2,146,375 | 2/1939 | Landis | 132/92 R |
| 2,354,454 | 7/1944 | Geffner | 132/91 |
| 2,664,093 | 12/1953 | Carpenter | 132/91 |
| 2,872,929 | 2/1959 | Rice | 132/91 R |
| 4,031,909 | 6/1977 | Kelley | 132/91 |
| 4,094,328 | 6/1978 | Ray | 132/91 |

Primary Examiner—Robert P. Swiatek
Assistant Examiner—Carolyn A. Harrison
Attorney, Agent, or Firm—Jack C. Munro

[57] ABSTRACT

A dental flossing tool which is constructed to utilize the conventionally available dental floss containing containers. The tool includes a support for the container. The tool also has an elongated member which is bifurcated at its outer end. Openings are formed within the legs of the bifurcated end. Dental floss is to be strung from the container along the surface of the elongated member through the openings resulting in the dental floss being tautly stretched across the legs. The free end of the dental floss is tightly wrapped around a protruding member which is integrally formed on the surface of the elongated member. The protruding member also includes a restrictor which restricts the pulling movement of the strand through the tool to facilitate tautly stretching of the dental floss across the gap.

5 Claims, 21 Drawing Figures

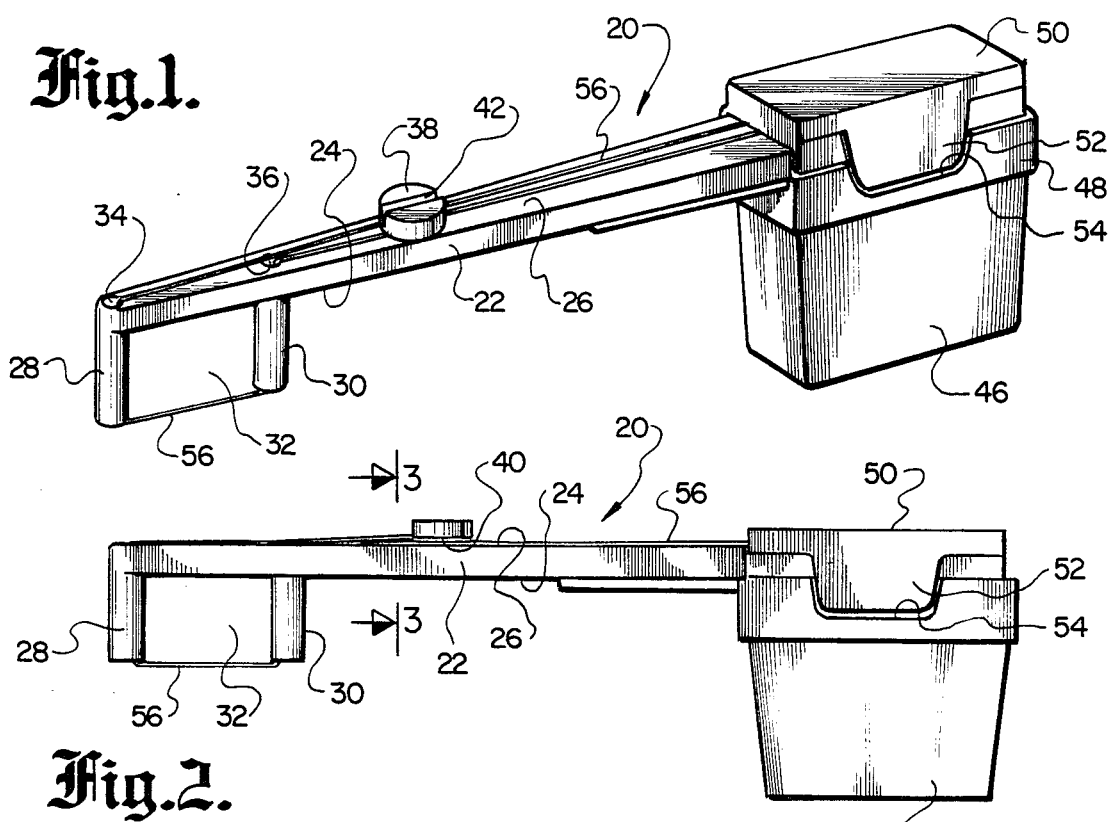
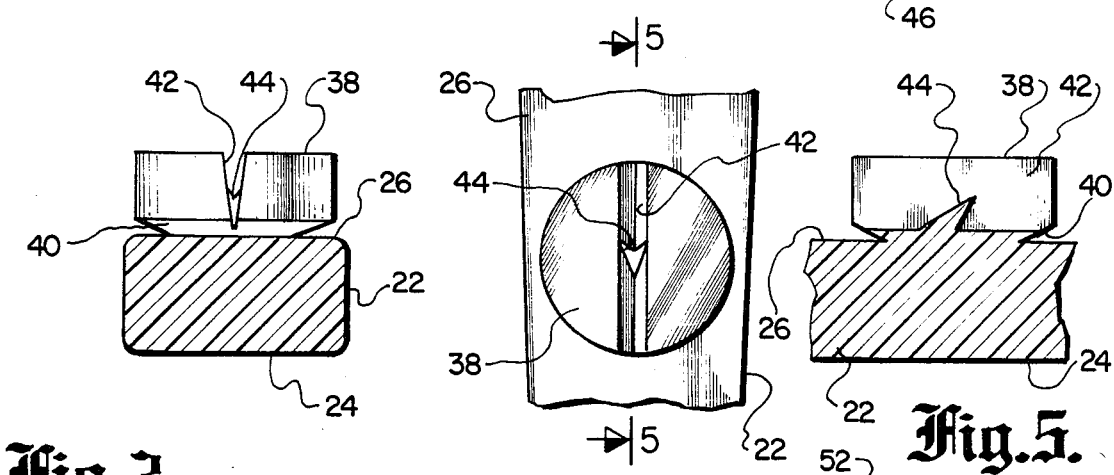
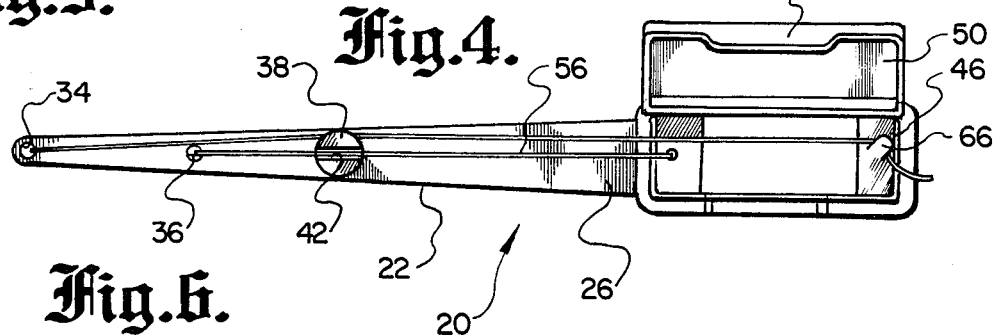

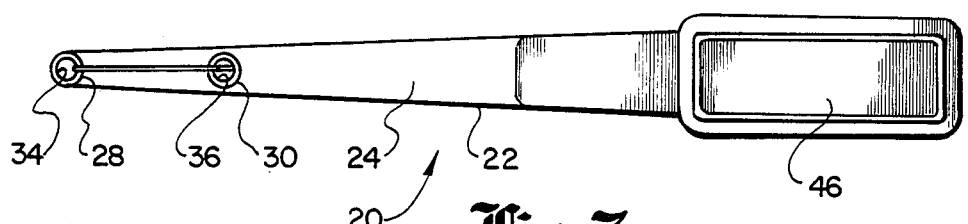
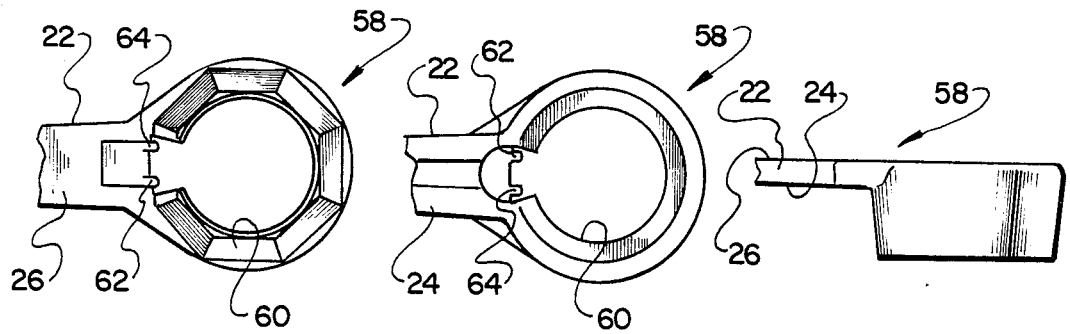
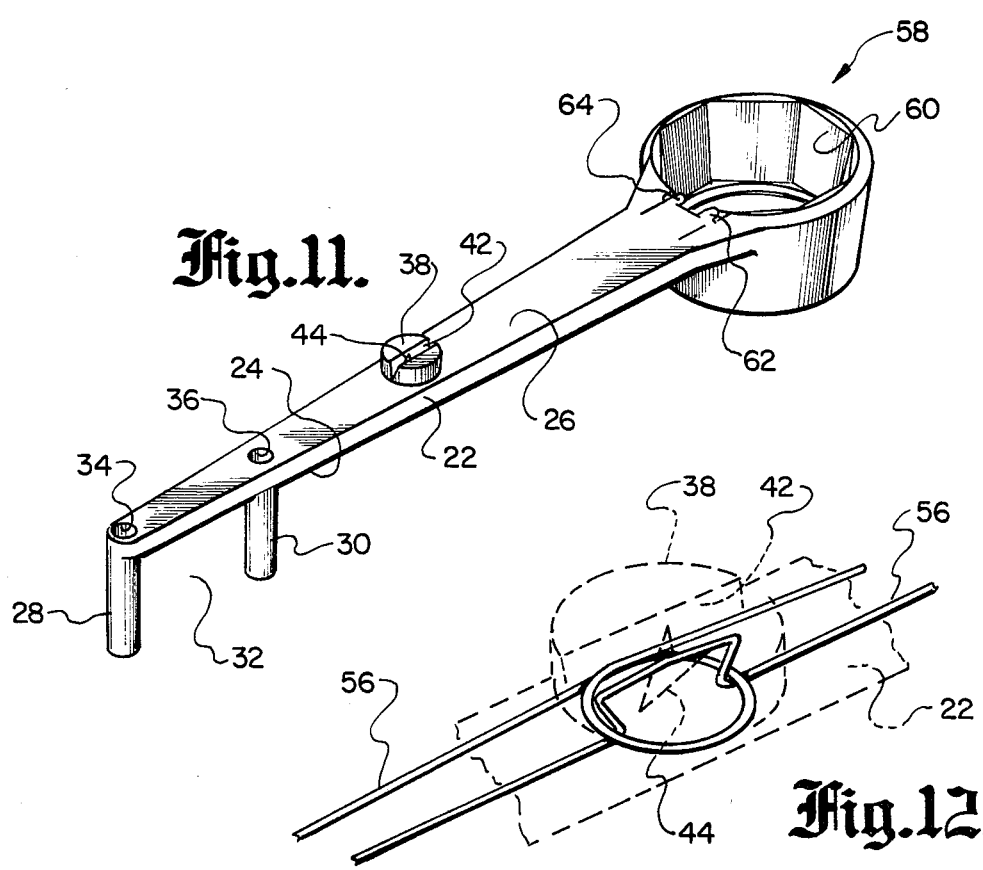

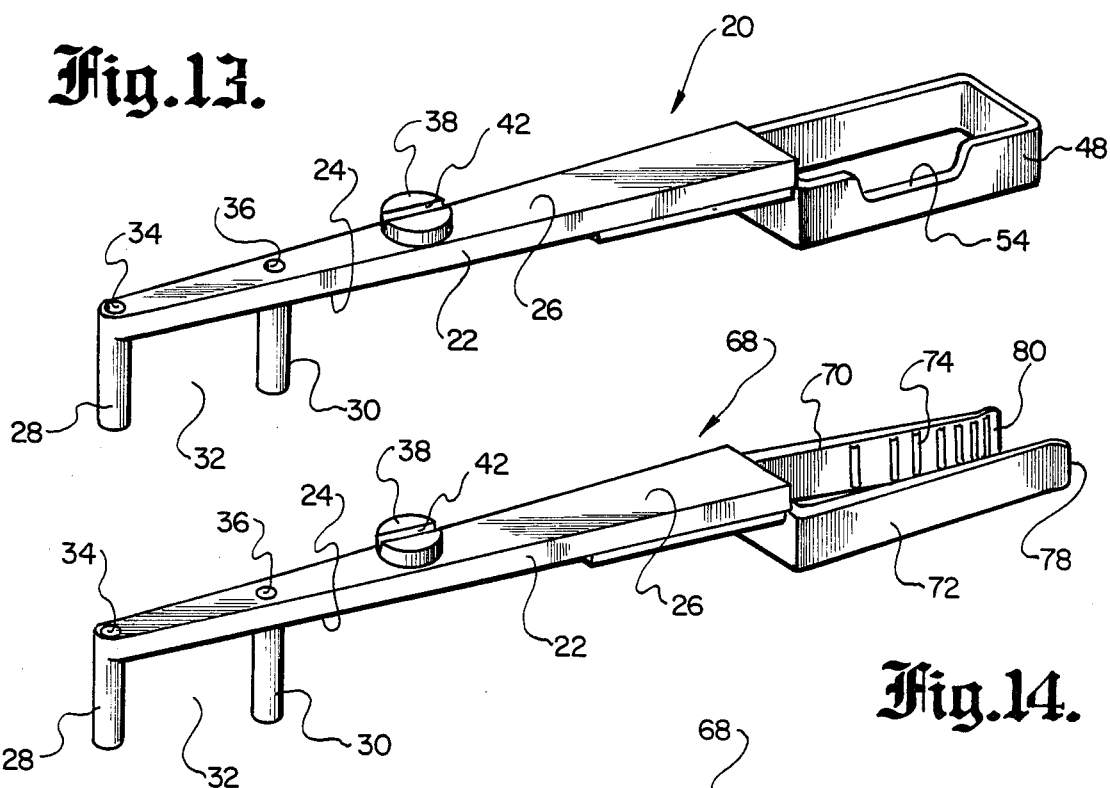
Fig.13.
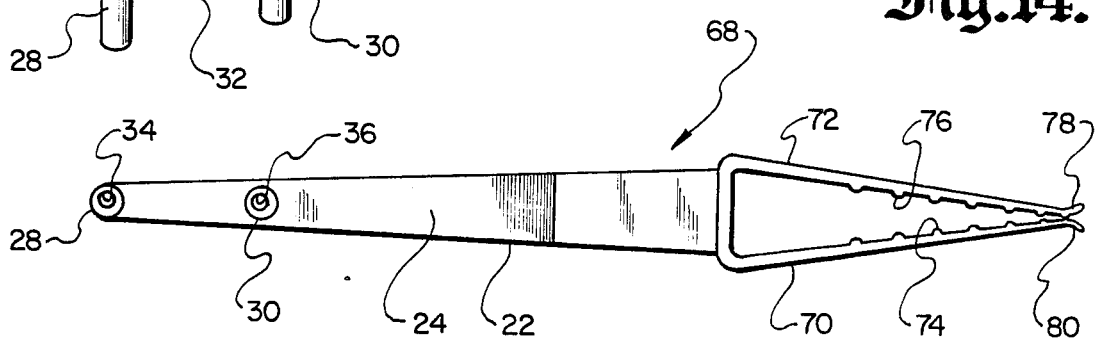
Fig.14.
Fig.15.

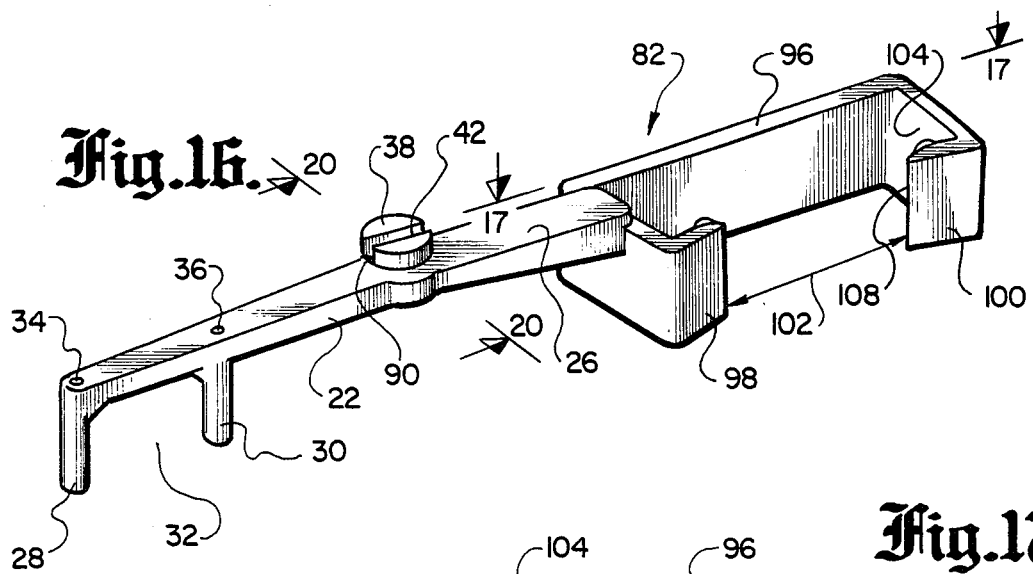
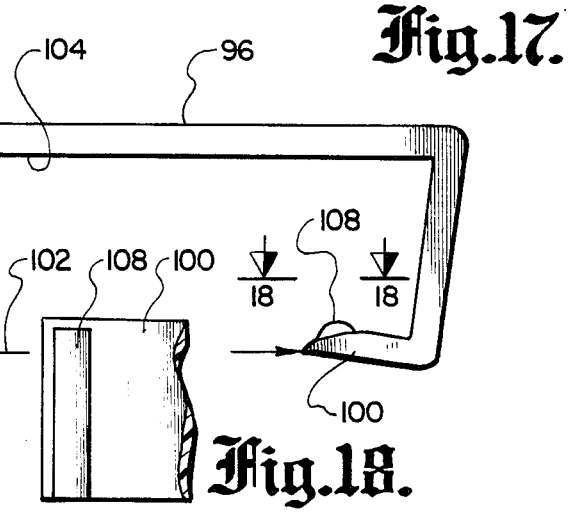
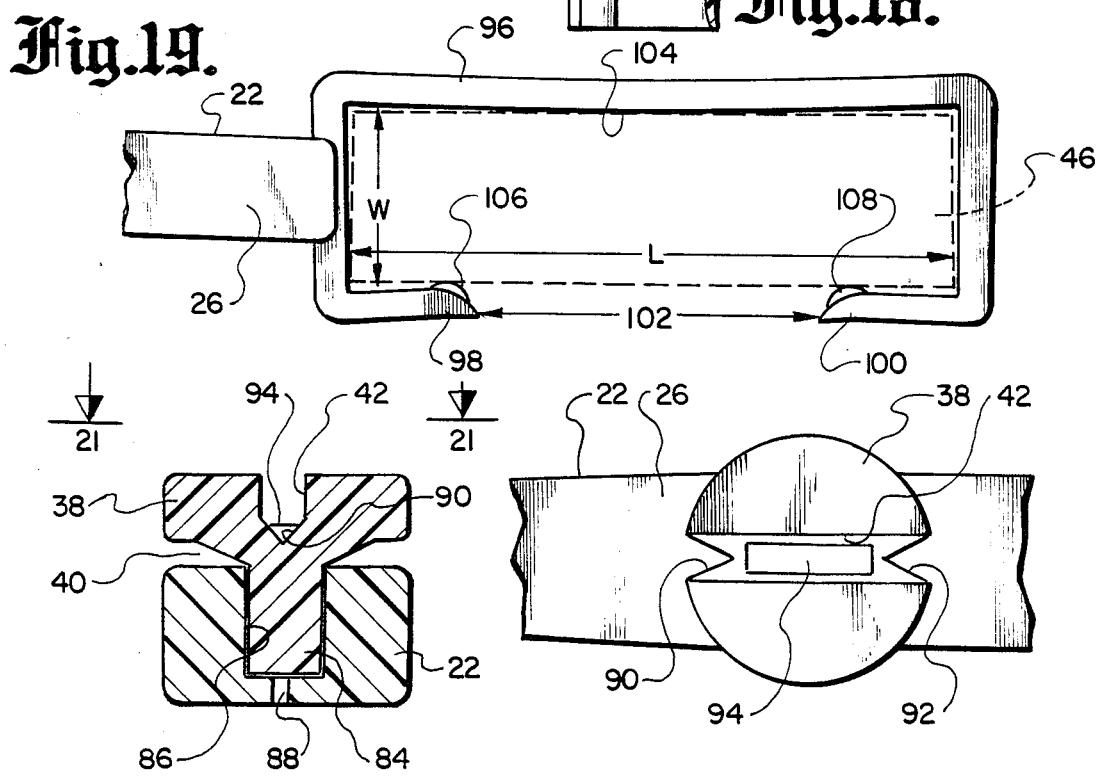

DENTAL FLOSSING TOOL

REFERENCE TO PRIOR APPLICATION

The subject matter of the present application is a continuation-in-part of patent application Ser. No. 413,682, filed Sept. 1, 1982, entitled, DENTAL FLOSSING TOOL by the present inventors, and now abandoned.

BACKGROUND OF THE INVENTION

The field of this invention relates generally to devices used by people for removing particles of food and the like from between their teeth through the use of a string which is drawn between a pair of directly adjacent teeth and moved in a reciprocal motion to effect cleaning of the area between the teeth.

Dental hygiene is of similar importance in peridontal disease. Dental flossing is an important ally of the toothbrush, since it may be passed through two adjoining teeth to remove hidden debris, particularly food particles which have been wedged between the teeth. Dental flossing is also helpful when cleaning the edges of the gums between the teeth and in preventing and removal of plaque which forms around the base of the teeth and causes serious gum disorders.

The most common way of dental flossing is for the individual to cut off a length of floss from a dispenser and introduce the length of floss into the mouth with the individual holding the strand of floss taut. However, flossing in this manner requires considerable coordination and perseverance. This procedure is not only time consuming, since a complete set of teeth has twenty eight areas between teeth, also putting of one's fingers in one's mouth is not the most desirable of experiences. Not only is it normally inherently distasteful to locate one's fingers in one's mouth, some people are employed in jobs which cause their hands to become deeply stained with contaminants or odorants which makes it physically distasteful for them to place their fingers into their mouths. For example, the hands of an automobile service station worker may become deeply grimed with carbon and the strong odor of gasoline.

Still further, the physical working area within one's mouth is confined. The physical size of one's fingers are normally too large to facilitate usage of dental floss within one's mouth.

Previously, there have been attempts to design a tool to achieve the purpose of dental flossing. The most common type of tool comprises a pair of protruding prongs which extend from a handle section. An individual is to remove a section of floss from a separate dispenser and attach the removed section of floss to the tool. Frequently, a single strand of dental floss will only work between a single pair of teeth. This means that during one complete usage, an individual with a full set of teeth, will be required to load and unload this dispenser twenty eight different times. As a result, although the tool itself will eliminate the inserting of one's fingers into one's mouth, it definitely does not facilitate the task of flossing, but actually complicates it and makes the flossing time greater.

At the present time, most dental floss is sold in some form of a container. Prior to the present invention, there has not been known any dental flossing tool which has been designed to be utilized in conjunction with a conventionally available dental flossing container.

SUMMARY OF THE INVENTION

One of the primary objectives of this invention is to construct a dental flossing tool which is to be utilized in conjunction with conventionally available dental flossing containers.

Another objective of this invention is to construct a tool which can be produced from a mold in a single shot and does not incorporate any moving parts.

Another objective of this invention is to construct a dental flossing tool which can be manufactured most inexpensively.

Another objective of this invention is to construct a dental flossing tool which will facilitate flossing almost anywhere, such as at one's home, at the office, riding in an automobile, etc.

Another objective of this invention is to construct a dental flossing tool which is small in size and can be readily carried in one's pocket or purse.

Another objective of this invention is to construct a dental flossing tool which can be sold most inexpensively so each individual can have his or her own dental flossing tool in the same manner that each individual has their own toothbrush.

The dental flossing tool of the present invention comprises an elongated member which has a fore end and an aft end. Within the aft end there is located a frame which is designed to accommodate a specifically designed, conventional dental flossing container. Once the container is installed within the frame, the strand of dental floss is to be dispensed from the container and extended across the elongated member and threaded through and between a pair of spaced-apart members. The dental floss extends across the gap between the members. Mounted on the elongated member between the frame and the pair of spaced apart members is a button shaped protuberance. Through the side wall of this protuberance there if formed an annular wedge shaped groove.

A slot is located substantially perpendicular to the groove and is formed within the protuberance dividing the groove into substantially two equal parts. Within the slot is located a wedge shaped ridge. The strand of dental floss is to be located within the slot in contact with the wedge shaped ridge which then functions as a restrictor to retard pulling movement of the dental floss which facilitates the stretching taut of the dental floss across the gap. The free end of the strand of dental floss is to be wrapped around the protuberance moving within the annular groove also forcing segments of the strand into the groove which are located directly adjacent the protuberance.

BRIEF DESCRIPTION OF THE DRAWINGS

FIG. 1 is an isometric view of the flossing tool of this invention which is designed to be utilized in conjunction with a box-like floss containing container;

FIG. 2 is a side elevational view of the flossing tool of FIG. 1;

FIG. 3 is a cross-sectional view taken along line 3—3 of FIG. 2;

FIG. 4 is a top plan view of the single protruding member mounted on the upper surface of the flossing tool of this invention which is utilized to tightly secure the strand of floss in place;

FIG. 5 is a cross-sectional view taken along line 5—5 of FIG. 4;

FIG. 6 is a top plan view of the flossing tool of this invention showing the floss containing container in an open position;

FIG. 7 is a bottom plan view of the floss containing container of FIG. 1;

FIG. 8 is a top plan view of a first modified version of flossing tool of this invention;

FIG. 9 is a bottom plan view of the first modified version of flossing tool of FIG. 8;

FIG. 10 is a side elevational view of the first modified version of the flossing tool of FIG. 8;

FIG. 11 is an isometric view of the first modified version of flossing tool of FIG. 8;

FIG. 12 is a diagrammatic view showing the securing arrangement for the strand of floss in conjunction with the flossing tool of this invention;

FIG. 13 is a perspective view of the flossing tool of FIG. 1 with the floss containing container removed;

FIG. 14 is a second modified version of flossing tool of this invention;

FIG. 15 is a bottom plan view of the flossing tool of FIG. 14;

FIG. 16 is a perspective view of a third modified version of the flossing tool of the present invention;

FIG. 17 is a top plan view of the container support section of this third modified version of the present invention taken along lines 17—17 of FIG. 16 showing the container support section in the position prior to connection with a dental flossing container;

FIG. 18 is a view of a portion of the container support section of the third modified version of the present invention taken along line 18—18 of FIG. 17;

FIG. 19 is a view similar to view 17 but showing the container support section in the position that it would be in when connected to a dental flossing container;

FIG. 20 is a cross-sectional view taken long line 20—20 of FIG. 16; and

FIG. 21 is a top plan view taken along line 21—21 of FIG. 20.

DETAILED DESCRIPTION OF THE SHOWN EMBODIMENT

Referring particularly to the drawings, there is shown in FIGS. 1 to 7, a dental flossing apparatus 20. The dental flossing apparatus 20 is constructed of an elongated member 22 which has a lower surface 24 and an upper surface 26. Integrally attached at the outermost end of the elongated member 22 and extending from the lower surface 24 is a first protruding member 28. Also integrally attached to the elongated member 22 and extending from the lower surface 24, is a second protruding member 30. The member 30 is spaced from the member 28 forming a gap 32 therebetween. The members 28 and 30 are normally of the same length with the preferable length being three-eighths to one-half of an inch. It is to be understood that the members 28 and 30, as well as the member 22 will be constructed of a rigid material, such as plastic.

A hole 34 is formed entirely through the member 28. A similar hole 36 is formed through the protruding member 30.

Integrally attached to the upper surface 26 of the member 22 intermediate its longitudinal length, is a single protruding member 38. The member 38 is basically in the shape of a button and includes an annular, wedge shaped groove 40 formed through the sidewall of the single protruding member 38. This wedge shaped groove 40 is positioned directly adjacent the top surface 26 of the elongated member 22.

The single protruding member 30 also includes a longitudinal slot 42. The longitudinal axis of the slot 42 is shown to be in substantial alignment with the longitudinal center axis of the member 22. Although this alignment, in most instances, will be preferred, it is considered to be within the scope of this invention that the slot 42 could be canted or inclined from this longitudinal axis.

The cross-sectional shape of the slot 42 is that of a vee. Within the V-shaped slot 42, there is located a V-shaped ridge 44. The V-shaped ridge 44 is inclined so that the apex of the V-shaped ridge 44 is located nearest the forward or outer end of the elongated member 22 (that is, the end that has the member 28 attached thereto). The reason for the ridge 44 will become apparent further on in the description.

The foregoing description applies equally as well to the structure shown within FIGS. 8-12. The only difference between the structures of FIGS. 1-7 and 8-12 is that the aft, or rear end, of each of the members is designed to accommodate a particular shape of floss containing container. Referring particularly to FIGS. 1-7, the flossing tool 20 is designed to be utilized in conjunction with a box-like floss containing container 46. This container 46 is deemed to be conventional and forms no specific part of this invention. Within FIGS. 8-12, the flossing tool is to be utilized with an octagonal shaped floss containing container (not shown).

Referring particularly to FIGS. 1-7, a band 48 is integrally attached to the elongated member 22. A top plan view of the band 48 is basically rectangular in shape and the floss containing container 46 is adapted to be inserted within the confines of the band 48. The floss containing container has a lid 50, with the flap 52 to facilitate opening of the lid 50. In order to accommodate and avoid interference of the flap 52 with the band 48, there is included a recess 54 within the band 48.

A strand 56 of floss is to be pulled from the container 46 and located within the slot 42. The strand 56 is then passed through the opening 36 across the gap 32 and through the opening 34 and then wound about the single protruding member 38 being located within the wedging groove 40. The portion of the strand located prior to the gap 32 is defined as the inner end, with the portion extending from the gap 32 being defined as the outer end. The floss across the gap 32 is parallel to the longitudinal center axis of the elongated member 22. This has been found to be preferable for usage, as the user's hand and arm movement is more natural to oscillate in this direction rather than lateral to the longitudinal center axis of the member 22. Movement of the strand across the gap 32 is retarded, or restricted, by means of the ridge 44 which inherently tends to resist this movement. This tends to keep the strand taut across the gap 32. The wrapping of the strand 56 about the protruding member 36 causes the portion of the strand on each side of the slot 42 to be also forced within the wedging groove 40. As a result, the ends of the strand are tightly secured together and held in place about the single protruding member 38, therefore tending to maintain the strand 56 secured in a taut manner across the gap 32.

Within the first modified version 58 shown within FIGS. 8-12, of the flossing tool of this invention, the aft end of the elongated member 26 includes an octagonally shaped recess 60. Within the recess 60, there is to be located a conventional floss containing container of a similar exterior configuration. This floss containing container will be snapped and held in place by small protuberances 62 and 64, which are to just slightly overlap the top surface of the floss containing container. The floss within this floss containing container is to be threaded through the tool in precisely the same manner.

It is to be understood that the excess length of floss is to be normally severed by a cutter which is mounted on the top surface of the floss containing container. One such cutter 66 is shown within the container 46 within FIG. 6 of the drawings. It is also considered to be within the scope of this invention that when the floss is emptied from its respective container, that the container is to be removed and a new container connected to the flossing tool.

Referring particularly to FIGS. 14 and 15 of the drawing, there is shown a second modified version 68 of flossing tool of this invention. Similar numerals have been utilized to refer to similar parts. The main distinction regarding flossing tool 68 is that the aft end of the tool 68 is bifurcated forming a pair of spaced apart legs 70 and 72. The legs 70 and 72 are inherently resilient and when at rest are located so that their respective outer flared ends 80 and 78 are almost touching each other. The inner surface of the leg 70 includes serrations 74, with the inner surface of the leg including serrations 76.

The legs 70 and 72 are to be spread apart to accommodate a flossing container, such as container 46. The biasing action of the legs 70 and 72 will bind against the exterior surface of the container 46 holding such in a fixed position in the space between the legs 70 and 72. The serrations 74 and 76 are to assist in preventing accidental dislodgement of the container 46. The primary distinction of the tool 68 is that it accommodates to different sizes of flossing containers 46, where the flossing tool 20 is restricted to a particular size of flossing container. It is to be understood that the flossing container is to be readily removable from and replaceable within the tool 68.

Referring particularly to FIGS. 16 to 20 there is shown the third modified version 82 of the flossing tool of this invention. Like numerals have been utilized to refer to like parts in relation to FIGS. 1 to 7. Actually the structure within FIGS. 16 to 21 is quite similar to that of FIGS. 1 to 7 with the exception that the button 38, instead of being integral with the elongated member 22, is formed separate therefrom utilizing a lower pin-like extension 84. The extension 84 is to be locatable within a recess 86 in a snug fitting manner within the member 22. An air hole 88 is formed also within the member 22 connecting with the recess 86. The reason for the air hole 88 is, that when the pin 84 is forced into recess 86, that the air contained within the recess 86 is evacuated through the air hole 88 and into the ambient. It is to be understood that through normal practice there will usually be provided some form of adhesive to securely attach the pin 84 to the elongated member 22.

The protruding member 38 is modified somewhat within FIGS. 16 to 21. One modification is the elimination of the restricter 44. Also, the ends of the slot 42 define V-shaped recesses 90 and 92. In between the recesses 90 and 92 is located a planer ledge 94. It has been found that with the strand of dental floss resting on the ledge 94 and then wound and received within the wedge-shape groove 40, that the strand of dental floss will be tightly forced into V-shaped slots 90 and 92, thereby tightly securing in place the strand of dental floss and also stretching such tightly across the gap 32.

It has been found that the floss containing containers 46 vary slightly in size. Therefore, the band 48 is not capable of accommodating a slightly different size of floss containing container 46. In order to adjust to different sizes of floss containing containers, the container support structure in the form side wall 96 is utilized.

Side wall 96 is shown to be substantially U-shaped including inwardly extending free ends 98 and 100. Between the free ends 98 and 100 is located an opening 102. Each of the free ends 98 and 100 extend a small distance to within the area 104 which is enclosed by the side wall 96. Insertion of the dental floss container 46 within the area 104 will cause the free ends 90 and 100 to be biased outwardly, as is clearly shown in comparing FIG. 17 to FIG. 19. With the free ends 98 and 100 biased outwardly, the inner surface of such, in the form of respective protrusions 106 and 108, are biased into frictionally tight contact with the container 46. It is the function of the protrusions 106 and 108 to facilitate the frictional connection with the container 46. It has been found that by using the side wall 96 that the dental flossing tool 82 can accommodate variances as much as forty-thousandths of an inch in length (l) and thirty-thousandths of an inch in width (w).

What is claimed is:

1. In combination with a dental floss container, said container containing a quantity of dental floss which is to be dispensed therefrom as a single strand, a dental flossing tool comprising:

an elongated member having an aft end and a fore end, said elongated member having a longitudinal center axis;

container support means attached to said aft end, said container support means comprising a generally U-shaped side wall defining a substantially enclosed area for mounting in a fixed position said dental floss container, said container support means including adjustment means for tight connection of said dental flossing tool to various sizes of said dental floss container, said adjustment means comprising an opening formed within said U-shaped side wall creating a free end of said side wall on each side of said opening, each said free end being deflectable outwardly during insertion of said dental flosser container into said enclosed area to increase the size of said enclosed area to accommodate to the specific size of said dental floss container, upon insertion of said dental floss container within said enclosed area said free ends being biased into tight contact with said dental floss container tightly gripping said dental floss container;

first means located at said fore end forming a gap, said first means comprising a pair of spaced-apart members, said pair of spaced-apart members extending from said elongated member, said strand to be tightly stretched across said gap, the portion of said strand located prior to said first means being defined as said inner end and the portion of said strand extending from said first means being defined as said outer end; and second means mounted on said elongated member for securing together said inner end and said outer end, said second means comprising a single member protruding from said elongated member, said inner end of said strand to be in contact with said single protruding member, said outer end to be wound around said single protruding member overlappingly engaging said inner end of said strand tightly securing said strand to said single protruding member and maintaining said strand in said tightly stretched condition across said gap.

2. The combination as defined in claim 1 wherein said single protruding member includes:
   an annular wedge shaped groove, said outer end of said strand to be located within said wedge shaped groove when wound about said single protruding member and a portion of said inner end to be also forced within said wedge shaped groove.

3. The combination as defined in claim 1 wherein:
   each said member of said pair of spaced apart members having an opening formed therethrough, said strand being conducted through said openings.

4. The combination as defined in claim 1 wherein:
   said strand across said gap being parallel to said longitudinal center axis.

5. The combination as defined in claim 2 wherein:
   each said free end including a protrusion to directly contact said dental floss container to facilitate frictional engagement with said dental floss container.

* * * * *